United States Patent [19]

Hillstead et al.

[11] Patent Number: 5,509,908
[45] Date of Patent: Apr. 23, 1996

[54] ANGULAR SHEATH INTRODUCER

[75] Inventors: Richard A. Hillstead, Duluth, Ga.; Joseph B. Muhlestein, Bountiful, Utah

[73] Assignee: Novoste Corporation, Norcross, Ga.

[21] Appl. No.: 230,614

[22] Filed: Apr. 21, 1994

[51] Int. Cl.[6] .................................................. A61M 5/00
[52] U.S. Cl. ........................ 604/264; 604/164; 604/167; 604/169; 604/171; 604/284
[58] Field of Search .............................. 128/772; 604/27, 604/43, 44, 45, 158, 159, 160, 161, 162, 163, 164, 165, 166, 167, 169, 170, 171, 264, 280, 284; 606/108

[56] References Cited

U.S. PATENT DOCUMENTS

| | | |
|---|---|---|
| 3,017,887 | 1/1972 | Heyer . |
| 3,875,938 | 4/1975 | Mellor ...................................... 604/167 |
| 4,000,739 | 1/1977 | Stevens . |
| 4,424,833 | 1/1984 | Spector et al. . |
| 4,573,865 | 3/1986 | Russo ........................................ 604/43 |
| 4,610,665 | 9/1986 | Matsumoto et al. . |
| 4,686,977 | 8/1987 | Cosma . |
| 4,798,594 | 1/1989 | Hillstead . |
| 4,874,365 | 10/1989 | Frederick et al. ...................... 604/165 |
| 4,874,378 | 10/1989 | Hillstead . |
| 4,895,565 | 1/1990 | Hillstead . |
| 4,960,412 | 10/1990 | Fink ........................................... 604/167 |
| 5,059,186 | 10/1991 | Yamamoto et al. . |
| 5,066,285 | 11/1991 | Hillstead . |
| 5,069,665 | 12/1991 | Ng ............................................. 604/164 |
| 5,112,308 | 5/1992 | Olsen et al. . |
| 5,125,902 | 6/1992 | Berry et al. . |
| 5,146,925 | 9/1992 | Snow . |
| 5,167,645 | 12/1992 | Castillo . |
| 5,219,335 | 6/1993 | Willard et al. . |
| 5,250,038 | 10/1993 | Melker et al. ........................... 604/264 |
| 5,290,244 | 3/1994 | Moonka ................................... 604/164 |

OTHER PUBLICATIONS

Conn, Harold (1993) Hepatology vol. 17, No. 1, p. 148, Transjugular Intrahepatic Portal–Systemic Shunts: The State of the Art.

*Primary Examiner*—Corrine M. Maglione
*Assistant Examiner*—N. Kent Gring
*Attorney, Agent, or Firm*—Bernstein & Associates

[57] ABSTRACT

A sheath introducer for a catheterization or similar procedure comprises a body having a upper portion and a lower portion, the lower portion being angled with respect to the upper portion; a curved tapering channel extending through the upper and lower portions; a cannula with a tapered distal end extending at an angle with respect to the upper portion a hemostatic valve having an access port and a fluid tight slit opening and seated within the upper portion and maintained by a cap; and an angled sideport in fluid communication with the channel. Optionally, a wiper flange extends inward within the valve access port which provide an additional fluid tight seal when a catheter is slidingly inserted, removed or maintained within the valve. A dilator can be adapted for use with the introducer by having a bend in the tube portion of the dilator.

15 Claims, 6 Drawing Sheets

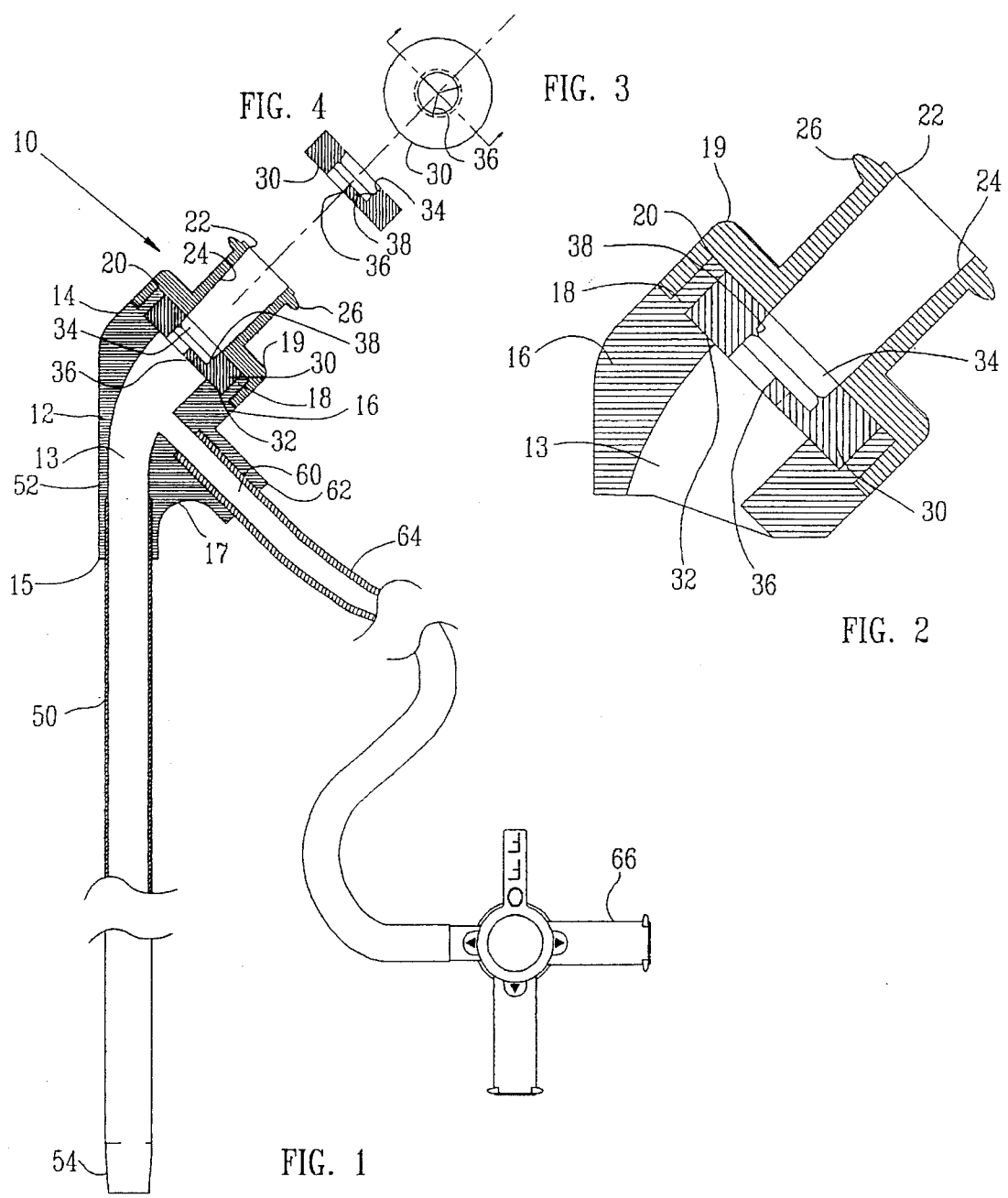

ANGULAR SHEATH INTRODUCER

FIELD OF THE INVENTION

The present invention relates to a hemostatic sheath introducer, and more particularly to a sheath introducer that can slidingly receive catheters or other similar devices after being inserted into a vessel while providing an improved angle for inserting and manipulating a catheter.

BACKGROUND OF THE ART

Hemostatic sheath introducers are well known in the art as devices for facilitating insertion, removal and manipulation of stents, catheters or like devices into a vein or artery. A procedure has been developed called Transjugular Intrahepatic Portalsystemic Shunts (TIPS), in which a catheter is inserted into the jugular vein via a sheath introducer. A sheath introduced is an access device comprising a cannula with fluid barrier valve and an access port. The cannula portion is inserted into a patient's blood vessel, typically an artery, and a number of different devices are insertable into the sheath introducer and into the vessel with an objective being to cause minimal trauma to the vessel and surrounding area.

Intrahepatic portal-systemic shunts are artificial fistulas between branches of the portal vein and the systemic circulation in the substance of the liver. The insertion and deployment of such shunts are among the most complex procedures in interventional medicine. During the procedure a number of catheters or similar devices must be inserted into a blood vessel via the sheath introducer. Currently available sheath introducers, such as that described in U.S. Pat. No. 4,000,739, issued to Stevens, and its progeny, utilize a straight bodied sheath introducer and are normally used for insertion into certain areas of the body. Insertion of a cannula into the jugular vein involves a less flexible site because the curved jaw and neck area provide awkward placement of a sheath introducer relative to the patient's body.

The sheath introducer of Stevens utilizes a straight body and co-axially aligned cannula, with a tapering body portion integrating with the cannula. Because the cannula is mounted in the center of the bottom of the body, this sheath introducer design has a disadvantage that when it is inserted into the vessel the body of the introducer can lift the cannula away from the surface of skin area, possibly causing stress and trauma to the vessel underneath and kinking the introducer cannula. Additionally, the access port is co-axially aligned with the cannula requiring insertion of catheters to be made substantially horizontal to the skin and a catheter may be difficult to insert where the cannula is inserted near the uneven topography of the jaw and neck region. It would be desirable to have a cannula that would angle away from the skin to permit more facile insertion of a catheter and reduce pulling and trauma to the vessel during insertion. It would also be desirable to have a cannula that extended eccentrically from the body of the introducer to minimize bending of the cannula with respect to the vessel and to prevent or reduce the likelihood of kinking the cannula.

SUMMARY OF THE INVENTION

The present invention provides a hemostatic sheath introducer suitable for TIPS and other catheterization procedures where an angled access port is useful.

Generally described, the present invention provides a generally cylindrical body with a top, a bottom and a sidewall, a portion of the body being at an angle, the body having a curved channel extending eccentrically therethrough tapering from the top to the bottom; a cannula extending from a peripheral portion of the bottom of the body and in fluid communication with the channel, the distal end of the cannula being slightly tapered; a cap fitted onto the top and having a housing within which fits a hemostatic valve; and, a sideport channel in fluid communication with the channel and in communication with a boss extending outward from the sidewall, the boss being connectable to a stopcock or other device by a tube. In one embodiment of the invention the boss is angled slightly downward toward the bottom corner of the body and preferably rotated 90° about the axis of the body. The valve can have an opening extending partially therethrough and a Y-slit which forms a penetrable fluid tight seal.

A dilator designed for use with the present invention is angled at the upper portion of the dilator body to more securely fit within the body of the sheath introducer. Such a dilator design provides an easier insertion and fit within the sheath introducer.

Accordingly, it is a principal object of the present invention to provide a hemostatic sheath introducer that affords increased access to the access port.

It is a further object of the present invention to provide a hemostatic sheath introducer that reduces trauma to the skin and vessel.

It is another object of the present invention to provide a hemostatic sheath introducer that has an eccentrically positioned cannula with respect to the body so as to lie closer to the skin when in an inserted position.

It is still a further object of the present invention to provide a hemostatic sheath introducer that reduces the likelihood of kinking the cannula during catheter manipulation.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which:

FIG. 1 is a side cutaway view of a preferred embodiment of the sheath introducer of the present invention.

FIG. 2 is a side cutaway detail view of the top of the body, the valve and the cap.

FIG. 3 is a top view of the hemostatic valve.

FIG. 4 is a side cutaway view of the hemostatic valve.

DESCRIPTION OF THE PREFERRED EMBODIMENTS

Figure 5:
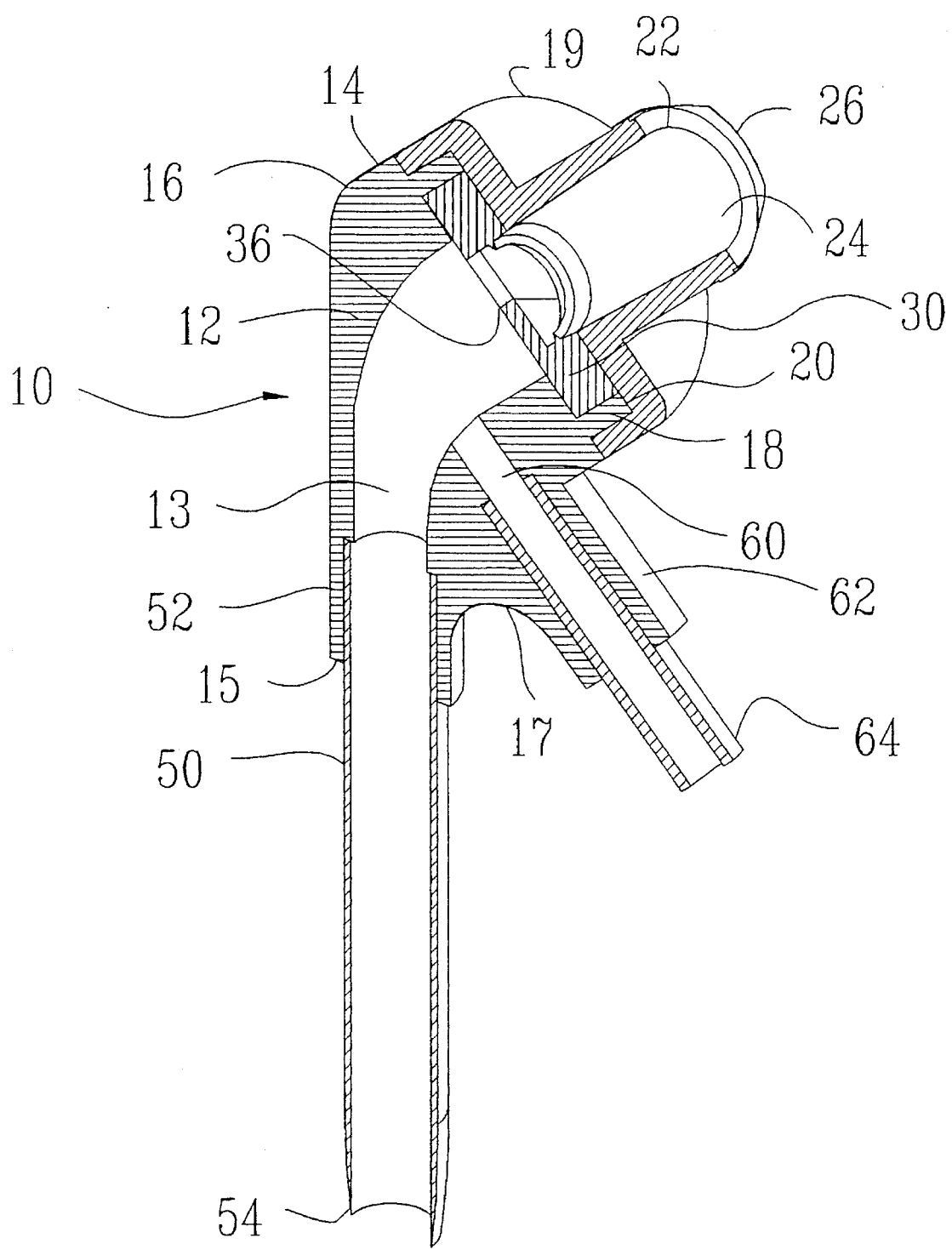
FIG. 5 is a side perspective view in partial cutaway of the sheath introducer.

FIGS. 1–7 shows a sheath introducer 10 according to a preferred embodiment in which a generally cylindrical body portion 12 has a top 14 and a bottom 15. The body contains first portion 16 and a second portion 17 which is at an angle with respect to the first portion 16. A preferred angle is 45°, but other angles are contemplated as being useable in the present invention. The body 12 contains a curved catheter channel 13 that tapers from the top 14 to the bottom 15. A ring 18 extends from the top 14. A cap 19 is snap fitted or bonded to the top 14 by being fitted over the ring 18 and fitted over a shoulder 20. The cap 19 has an access port 22, the inner wall 24 of which is a standard or modified luer taper. A luer thread 26 extends from the exterior of the cap 19.

The body 12 is preferably made of any of a number of suitable materials, such as high density polyethylene. The material should be rigid, biocompatible and cleanable.

An elastomeric unitary disc-shaped hemostatic valve 30 is seated within the ring 18 and rests on a shoulder 32 and comprises a centrally positioned access port hole 34 extending partially within the valve 30, and a Y-slit 36, as shown in FIGS. 3 and 4. Preferably, a beveled inward-protruding lip 38 extends annularly in the hole 34 which acts as an additional seal, enhancing the ability of the valve 30 to maintain hemostasis while catheters are being inserted, removed or maintained within the sheath introducer 10. The Y-slit 36 is aligned axially with the hole 34 and permits entry of a catheter 40 or similar device into the channel 13 through the hole 34 and forms a fluid-tight seal when no catheter is present and also when a catheter is inserted into the slit 36. The slit 36 also aligns the catheter 40 for reception within the channel 13.

A cannula 50 extends from the bottom 15 and is in fluid communication with the channel 13. The cannula 50 is at an angle with respect to the hole 34 and lies close to the back surface 52 of the body 12, In this manner the cannula 50 is off-axis with respect to the upper portion of the channel 13. The purpose of the offset cannula 50 is to maintain a closer alignment with the skin after positioning. The distal end 54 of the cannula 50 is tapered slightly for easier introduction into a vessel and to adhere closely to the exterior surface of a vessel dilator.

Figure 6:
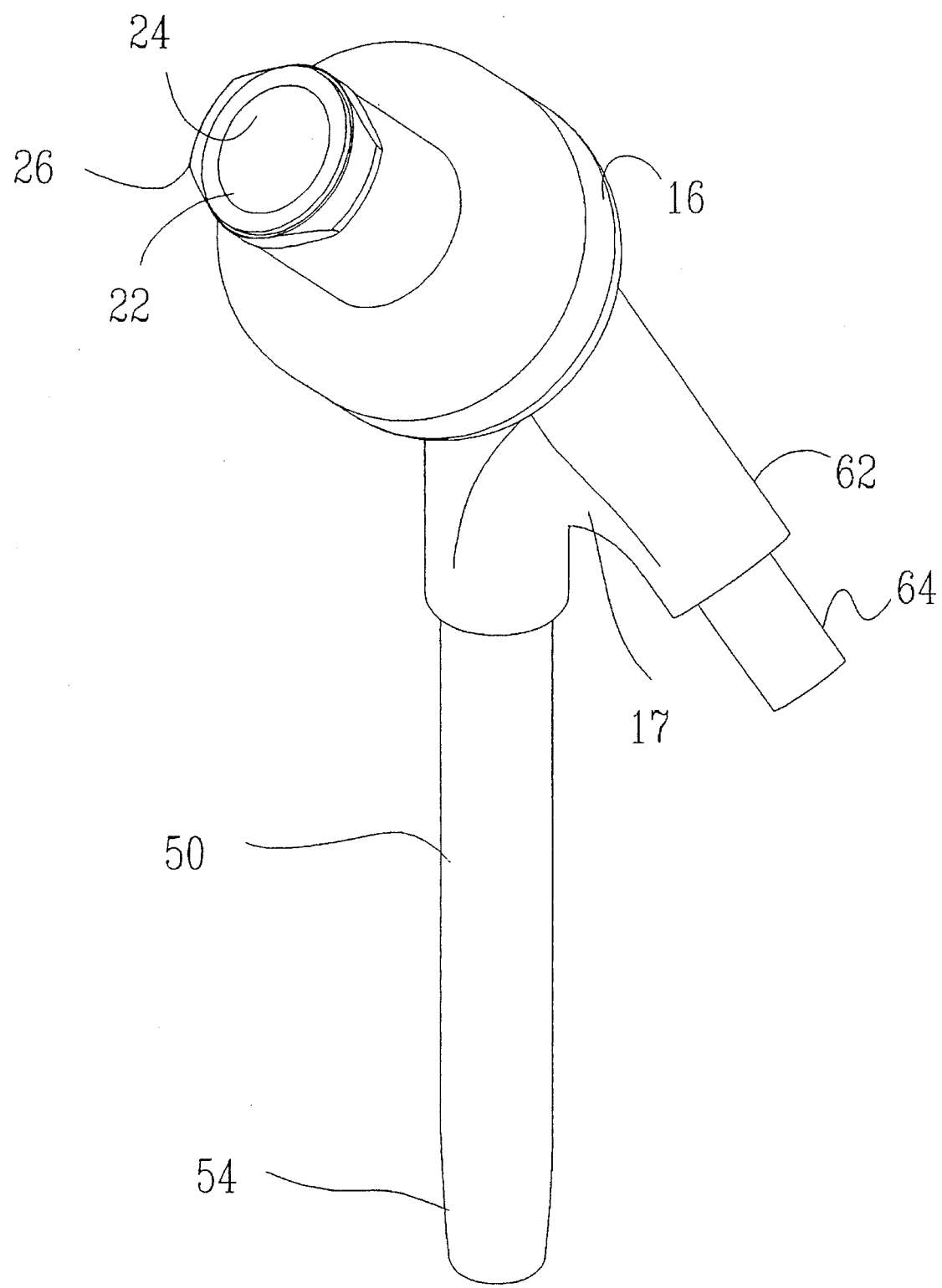
FIG. 6 is a front side perspective view.
Figure 7:
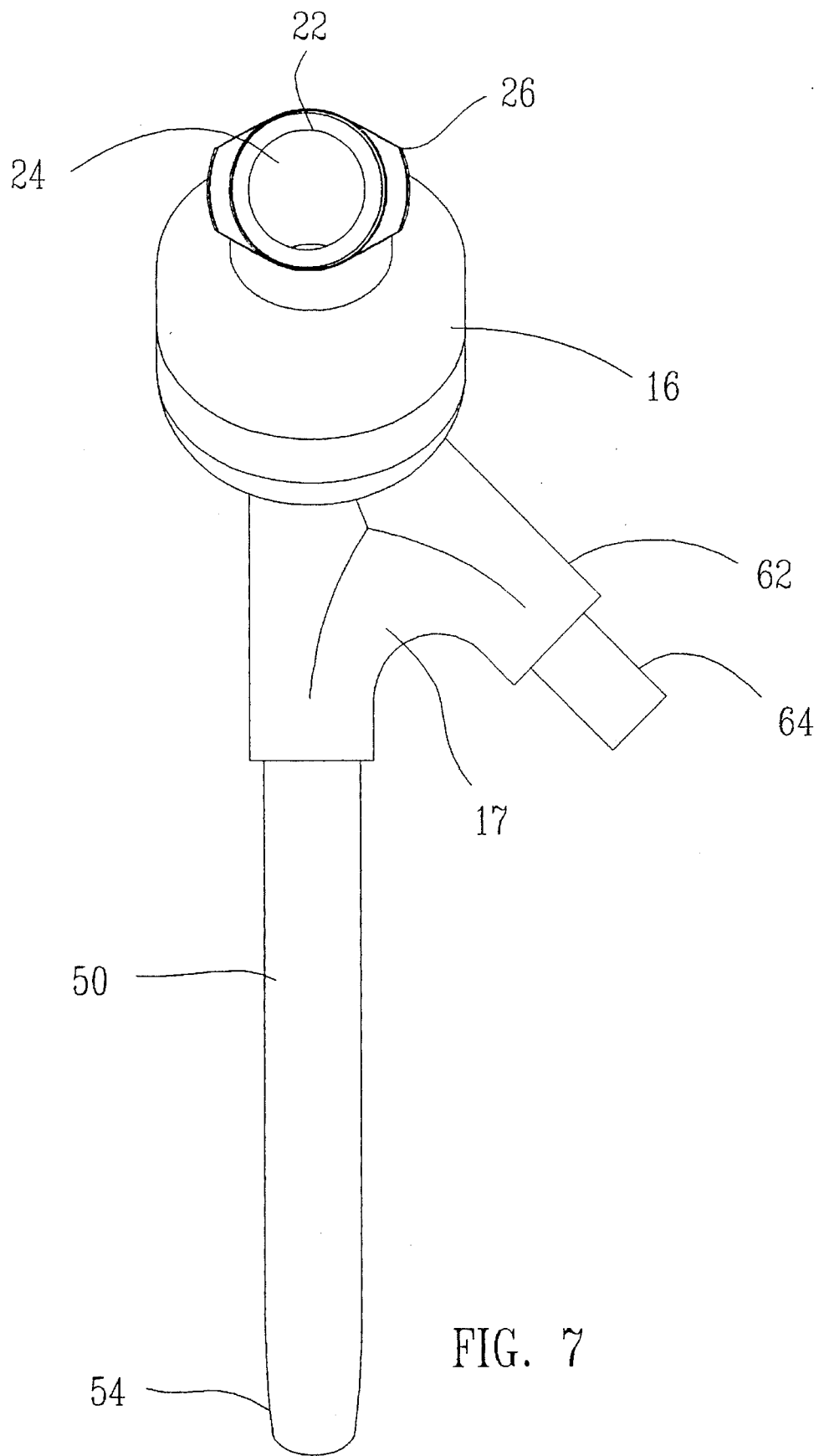
FIG. 7 is a back side perspective view.

A sideport channel 60 is in fluid communication with and extends from the channel 13 and is angled toward the bottom 15. A boss 62 extends downward toward the bottom 16, i.e., perpendicular with respect to the axis of the first portion 16 so as to prevent the tubing 64 from possibly interfering with any insertion operations at the top 14 and is in fluid communication with the sideport channel 60 and connects to a sidepert tubing 64, which is connectable to a conventional stopcock 66 or other device. Optionally, as shown in FIGS. 6 and 7, the boss 62 is rotated about 90° (although any suitable angle will suffice) in order to be orthogonal with respect to the cannula and the top 14. It is also possible to eliminate the sideport channel 60 and boss 62 altogether, if desired.

Figure 8:
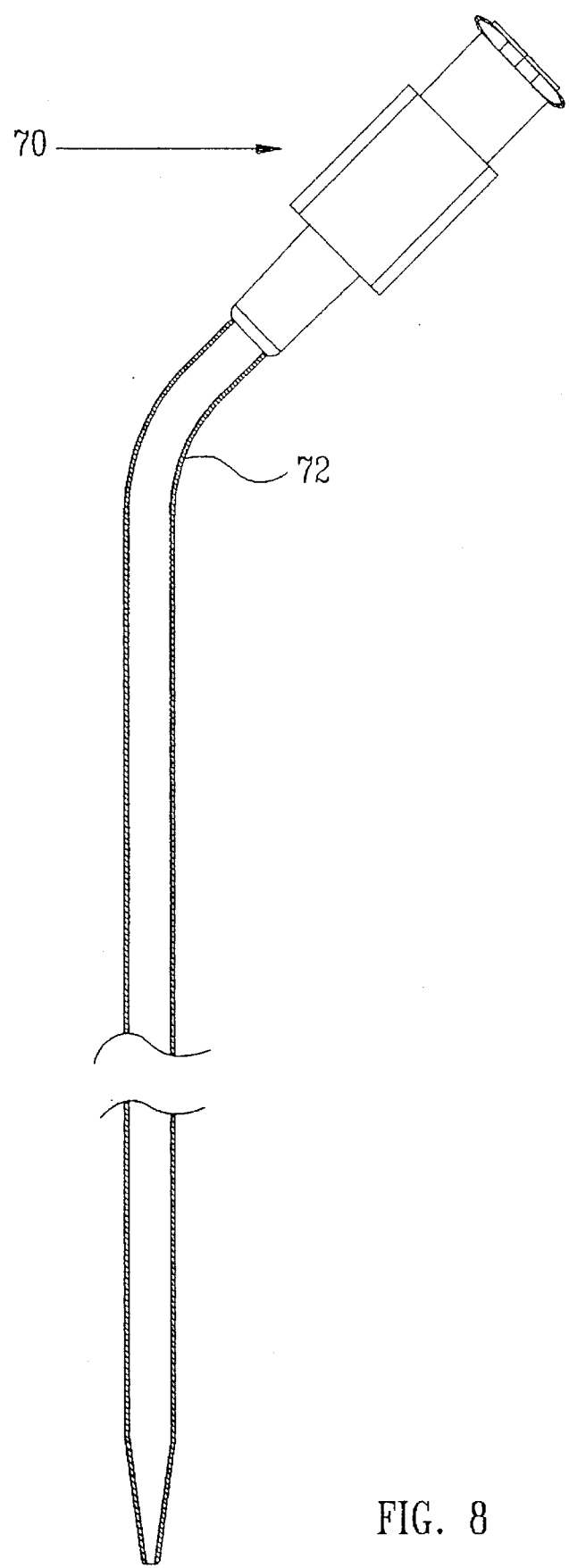
FIG. 8 is a side view in partial cutaway of an adapted angled dilator of the present invention.

A conventional straight dilator can be used or one can adapted for use with the present invention, as shown in FIG. 8, by molding a dilator 70 with an angled bend, generally designated at 72, which matches the angle of the body 12. The angled dilator 70 design permits easier introduction of the dilator into the sheath introducer 10 and reduces the possibility of kinking. Although the angle of the dilator 70 is not critical, it is desirable for the angle to be compatible with the angle of the body 12.

Figure 9:
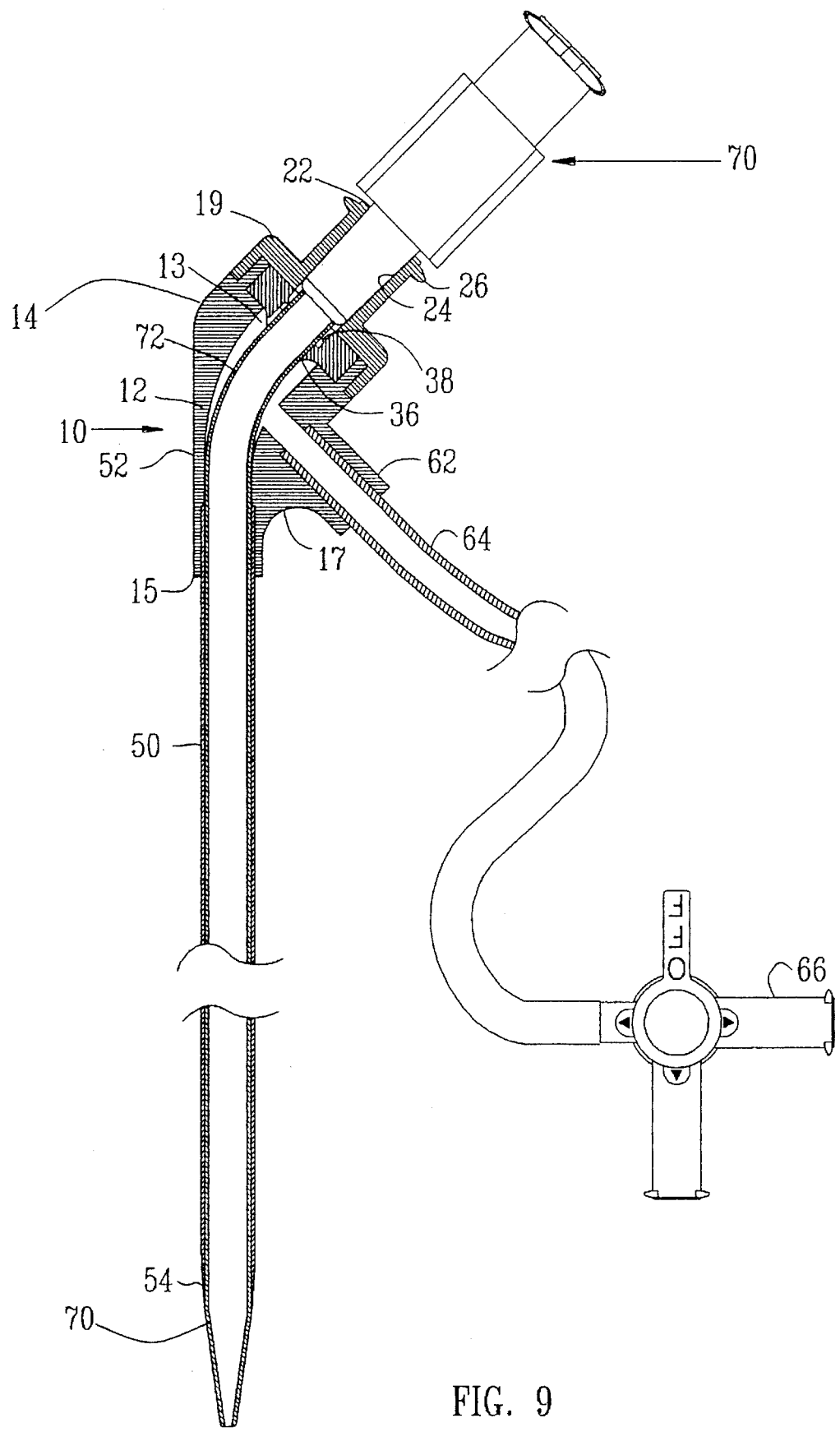
FIG. 9 is a side cutaway view of the sheath introducer with a dilator inserted into the cannula.

The sheath introducer 10 of the present invention is optimally used in a TIPS procedure although other catheterization procedures can employ the invention. Such procedures have been described in the literature and are well known in the art. Briefly, however, a blood vessel (such as the jugular) is located by palpating the skin above the desired vessel. A needle is inserted into the vessel. A guidewire is introduced through the needle and into the vessel. The needle is then removed leaving the guidewire in place. A vessel dilator 70 with a tapered end slides into a sheath introducer 10 via the hole 34 (as shown in FIG. 9) and both advance over the wire. The dilator 70 and sheath introducer 10 are then inserted into the vessel. The vessel dilator 70 and wire are then removed leaving the cannula 50 of the sheath introducer 10 remaining in the vessel.

While the sheath introducer 10 of the present invention is maintained at the entry site, other objects may be inserted and withdrawn from the access port 24, such as but not limited to stents, catheters, shunts, needles, syringes, and the like. The angled body 12 of the present invention permits easier insertion of objects into the hole 34 because the hole 34 is angled away from the skin and the neck area. It also improves catheter manipulation, patient comfort and reduces the likelihood of cannula damage or kinking. The offlet of the cannula 50 from the body 12 minimizes the bend between the body 12 and the skin. The angled and/or rotated sideport boss 62 permits unobstructed access to the hole 34.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

We claim:

1. A hemostatic sheath introducer, comprising:

a tubular body having a first curved lumen extending therethrough and a top and a bottom end said first lumen tapering from said top to said bottom, said top being angled with respect to said bottom;

a cap having an opening therein sized to be fitted onto said top end;

an elastomeric valve having an opening and a slit defined therein adapted for receiving an elongated member in a slidingly sealable relationship, said valve being receivable within said top and maintained in place by said cap;

a cannula extending from said bottom, said cannula being in fluid communication with said first lumen and said cannula being offset from the center of said body; and, a sideport comprising a second lumen extending laterally from said first lumen to said sidewall and a boss extending outward from a sideport comprising a second lumen extending laterally frown said first lumen and a boss extending outward from said body, and said second lumen being in fluid communication with said first lumen.

2. The sheath introducer of claim 1, wherein a portion of said cannula is tapered.

3. The sheath introducer of claim 1, wherein said slit is Y-shaped in cross-section and is capable of maintaining a fluid tight seal when a tube is slidingly inserted therein while permitting movement of said tube.

4. The sheath introducer of claim 1, wherein a tube is connected to said boss.

5. The sheath introducer of claim 4, wherein said tube is connected to a stopcock.

6. The sheath introducer of claim 1, wherein said boss is angled downward toward said bottom.

7. The sheath introducer of claim 1, wherein said opening of said valve has an annular inwardly protruding flange capable of forming a seal when an elongated tube member is slidingly inserted into said opening.

8. The sheath introducer of claim 7, wherein said elongated member is a catheter.

9. The sheath introducer of claim 1, wherein said cannula is angled at 45° with respect to said body.

10. The sheath introducer of claim 1 wherein said opening in said cap has a luer taper.

11. The sheath introducer of claim 1, wherein said cap has an exterior luer thread.

12. The sheath introducer of claim 1, further comprising a dilator comprising a body and a robe, said tube being slidingly receivable within said body and said cannula, said dilator having a portion of said tube being angled.

13. The sheath introducer of claim 12, wherein said angle of said dilator is 45°.

14. The sheath introducer of claim 1, wherein said boss is rotationally offset from said top.

15. The sheath introducer of claim 14, wherein said angle said boss is offset is 45°.

* * * * *